(12) United States Patent
Wong (10) Patent No.: US 8,222,606 B1
(45) Date of Patent: Jul. 17, 2012

(54) AIR SAMPLER FOR RECALIBRATION OF ABSORPTION BIASED DESIGNED NDIR GAS SENSORS

(75) Inventor: Jacob Y Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

(21) Appl. No.: 13/348,568

(22) Filed: Jan. 11, 2012

Related U.S. Application Data (63) Continuation-in-part of application No. 13/149,738, filed on May 31, 2011.

(51) Int. Cl.
*G01J 5/02* (2006.01)
(52) U.S. Cl. ............. 250/345; 250/343; 250/252.1; 73/23.2; 356/437
(58) Field of Classification Search .......... 78/31.02, 78/21.2, 23.21, 23.22, 1.02, 1.03; 250/338.5, 250/343, 344, 252.1, 345, 573, 346; 356/437, 356/440, 432, 433, 436, 246; 702/85; 422/83; 73/31.02, 21.2, 23.21, 23.22, 1.02, 1.03
See application file for complete search history.

(56) References Cited

U.S. PATENT DOCUMENTS

| | | | | |
|---|---|---|---|---|
| 5,874,737 | A * | 2/1999 | Bytyn et al. ............... | 250/343 |
| 6,753,967 | B2 * | 6/2004 | Stuttard .................... | 356/437 |
| 7,710,568 | B1 * | 5/2010 | Paige et al. ............... | 356/437 |
| 2006/0173637 | A1 * | 8/2006 | Martin ...................... | 702/24 |
| 2008/0185524 | A1 * | 8/2008 | Kanstad ................... | 250/338.5 |
| 2009/0008560 | A1 * | 1/2009 | Gunn et al. ............... | 250/343 |

* cited by examiner

*Primary Examiner* — David Porta
*Assistant Examiner* — Yara Green
(74) *Attorney, Agent, or Firm* — Roy L Anderson; Wagner, Anderson & Bright PC (57) ABSTRACT

The construct of a specially designed air sampler and its function in order to carry out the Effortless Recalibration (ERB) procedure to an Absorption Biased (AB) designed NDIR gas sensor with the use of a Calibration Master is described.

16 Claims, 10 Drawing Sheets

AIR SAMPLER FOR RECALIBRATION OF ABSORPTION BIASED DESIGNED NDIR GAS SENSORS

CROSS REFERENCE TO RELATED APPLICATIONS

This application is a continuation-in-part application of U.S. Ser. No. 13/149,738, filed May 31, 2011, the disclosure of which is specifically incorporated herein by reference.

FIELD OF THE INVENTION

The present invention is in the field of special apparatus used in conjunction with a method for re-calibrating Absorption Biased (AB) designed non-dispersive infrared (NDIR) gas sensors whose outputs have drifted over time and no longer correctly reflect their measurement accuracy.

BACKGROUND OF THE INVENTION

Output stability or drift over time leading to measurement inaccuracies has long been a major deficiency for gas sensors irrespective of what technology or methodology is used for their conception or realization. Output software correction may alleviate the problem somewhat but it is in many instances inaccurate and not even always applicable. Software correction has proven to be somewhat successful so far only to NDIR CO2 gas sensors used in Demand Control Ventilation application to save energy in the HVACR industry. It has long been the objective of many researchers in this field to overcome this problem fundamentally and for good. Recently the present author in U.S. application Ser. No. 12/859,749 advanced the teaching of an Absorption Biased NDIR Gas Sensing Methodology which is capable of eliminating substantially all NDIR gas sensor output drifts over time without the need for re-calibration (Wong, filed 19 Aug. 2010, now allowed to be issued 3 Jan. 2012). As it turns out, the solution to solving this output drift problem for gas sensors actually lies deeper than the availability of superior NDIR gas sensor types even though they can indeed be designed to be capable of maintaining measurement accuracy over time. The fact of the matter is that people have experienced gas sensor output instability for such a long time in the past that when output stable sensors really come along nobody will believe it. Until such time that stable gas sensors become widely available and users begin to consider their performance as trustworthy and truly believable, the real need today must be viewed at a completely different perspective and that is to be able to come up with a fast, inexpensive and simple methodology that can easily check the accuracy of gas sensors and, more importantly, just as easily and simply, hence inexpensive labor-wise, to re-calibrate them when they are found to be inaccurate.

Notwithstanding, the teaching of an Absorption Biased NDIR Gas Sensing Methodology by the present author in U.S. application Ser. No. 12/859,749 (Wong, filed 19 Aug. 2010, now allowed to be issued 3 Jan. 2012), only takes advantage of the invariance of the absorption Physics for NDIR gas measurement. As long as the changes of the sensor component characteristics over time does not affect the absorption Physics of NDIR gas measurement, the output of the sensor will remain significantly drift free. Such is the case for the aging characteristics of the infrared source whose Blackbody temperature tends to increase or decrease over time due to resistance changes causing the spectral content of its output to change. These spectral output changes can however be controlled by design by the Absorption Biased methodology not to affect the invariance of the absorption Physics for gas measurement and the outputs for such NDIR gas sensors can therefore remain significantly stable over time.

But there are situations when the changes of the sensor component characteristics alter the absorption Physics of gas measurement despite the application of the Absorption Biased methodology. When this happens, the absorption Physics invariance over time is broken and the output of the sensor will not remain stable over time. One such situation is for the filament of an incandescent infrared source (miniature light bulb) to physically sag over time. Another such situation is for a MicroElectrical Mechanical System (MEMS) infrared source to generate irregularities on its radiation emitting surface. In both cases, the ratio of the amount of radiation received by the Signal channel detector and that by the Reference channel detector is altered even when there is no gas of interest in the sample chamber thereby changing the invariance of the Absorption Physics for NDIR gas measurement. All told, it is almost impossible to design NDIR gas sensors even today whose outputs remain completely and indefinitely drift free over time. At some point in time in the future, the outputs of NDIR gas sensors will inevitably change due to the aging of sensor component characteristics affecting the invariance of the absorption Physics. It is therefore so very important to come up with a fast, inexpensive and simple methodology that can easily check the accuracy of NDIR gas sensors and more importantly, just as easily and simply, hence inexpensively labor-wise, to recalibrate them when they are found to be inaccurate.

The present author recently in U.S. application Ser. No. 13/149,738 advanced the teaching of a re-calibration methodology for Absorption Biased (AB) designed NDIR Gas Sensors (Wong, filed 31 May 2010) capable of easily and simply re-calibrating such NDIR gas sensors whose outputs have drifted over time and no longer correctly reflect their measurement accuracy. But this methodology only applies and works with Absorption Biased designed NDIR gas sensors as advanced by the present author in U.S. application Ser. No. 12/859,749 (Wong, filed 19 Aug. 2010, now allowed to be issued 3 Jan. 2012) and not with ordinary conventional NDIR nor other technology types of gas sensors. The disclosure of this re-calibration methodology for AB designed NDIR gas sensors just mentioned only dealt with the theoretical principle behind such a re-calibration technique. It is therefore the object the current invention to fill in the procedural details for carrying out such a task including the description of a special apparatus called an air sampler needed in order to perform such a re-calibration routine accurately all the time.

SUMMARY OF THE INVENTION

The present invention is generally directed to apparatuses and systems, and methods for their use, which allow an absorption biased ("AB") non-dispersive infrared ("NDIR") gas sensor to easily be recalibrated.

A calibration master NDIR gas sensor is used to calculate a calibration master gas concentration ("PCM") of a sample gas within a close environ air space of an AB NDIR gas sensor.

An air sampler, which can rely upon a substantially airtight telescopic sampling tube, obtains an air sample from a close environ air space in which the AB NDIR gas sensor is located.

An AB NDIR gas sensor calculates a gas concentration ("P") of the sample gas within the close environ air space through use of a calibration curve for the AB NDIR gas sensor, said calibration curve being obtained from a gamma ratio ("G") that has been normalized by the gamma ratio when no sample gas is present in the sample chamber ("G0") of the AB NDIR gas sensor, G being the ratio of a signal channel output ("VS") of the NDIR gas sensor divided by a reference channel output ("VR") of the NDIR gas sensor. The AB NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel pathlength. The AB NDIR gas sensor has no moving parts for effecting the interposition of spectral filters or an absorbing cell or a non-absorbing cell to create both the signal channel and the reference channel.

If a recalibration condition is detected, the AB NDIR gas sensor is recalibrated by comparing P to PCM and adjusting G0 based upon a reversed calibration curve algorithm.

The calibration master NDIR gas sensor (which can also be an AB NDIR gas sensor) communicates with the AB NDIR gas sensor, preferably wirelessly, and can send the AB NDIR gas sensor a recalibration command when the difference between P and PCM exceeds a preselected threshold. The calibration master can create a record of P, PCM, an identifier that uniquely identifies the AB NDIR gas sensor and a date associated with when the air sample was obtained.

It is therefore a primary object of the present invention to advance special apparatus used in conjunction with a method for re-calibrating Absorption Biased (AB) designed non-dispersive infrared (NDIR) gas sensors whose outputs have drifted over time and no longer correctly reflect their measurement accuracy.

This and further objects and advantages will be apparent to those skilled in the art in connection with the drawings and the detailed description of the invention set forth below.

DETAILED DESCRIPTION OF THE INVENTION

The present invention is preceded by the teaching of a design methodology for NDIR gas sensors capable of significantly reducing their output drifts over time disclosed in U.S. application Ser. No. 12/859,749 (Wong, filed 19 Aug. 2010, now allowed to be issued 3 Jan. 2012), which is specifically incorporated herein by reference. It is important to point out the fact that such a design methodology only applies to NDIR gas sensors and not to other technology types of gas sensors. The present invention complements the teaching of a re-calibration methodology advanced by the present author in Application No. 13/149,738 (Wong, filed 31 May 2010) capable of easily and simply re-calibrating Absorption Biased designed NDIR gas sensors. Before embarking into the detailed description of the present invention, it will clarify matters a lot by briefly reviewing the Physics behind the Absorption Biased (AB) methodology and the Re-calibration methodology applicable only to AB designed NDIR gas sensors.

By taking advantage of the fact that if the spectral content of radiation emanating from the source and/or subsequently convoluted with those from the surroundings are always kept the same for both the signal and the reference channels of a dual-beam NDIR gas sensor, the output of the sensor taken as the ratio of the signal output over the reference output can be kept significantly constant or invariable over time except when the gas of interest is present in the sample chamber. In order to do this, both the signal and the reference channel must be provided with exactly the same spectral narrow band-pass filter designed for detecting the gas of interest in front of their respective infrared detectors. In order to differentiate between the signal and the reference channel outputs from the respective detectors in the presence of the gas of interest, an absorption bias is designed into the two channels via the use of different sample chamber path lengths for the two channels. Thus, if the sample chamber path length for the signal channel is purposely designed to be longer than that for the reference channel, the signal channel detector output will decrease a lot more than that for the reference channel when there is a presence of the gas of interest in the sample chamber.

Because both detection channels have the same narrow band-pass spectral filter and they receive radiation from one and the same single infrared source, their outputs to first order have to be affected in the same way even when there are spectral changes caused by temperature variations in the sample chamber and/or by the short- or long-term operational changes of the infrared source. Thus, the outputs of such a dual-beam NDIR gas sensor for the detection of any gas of interest (not just CO2) implemented using the Absorption Biased (AB) methodology will stay substantially drift-free over time without the need for any periodic recalibration nor the implementation of any output correction software.

Figure 1:
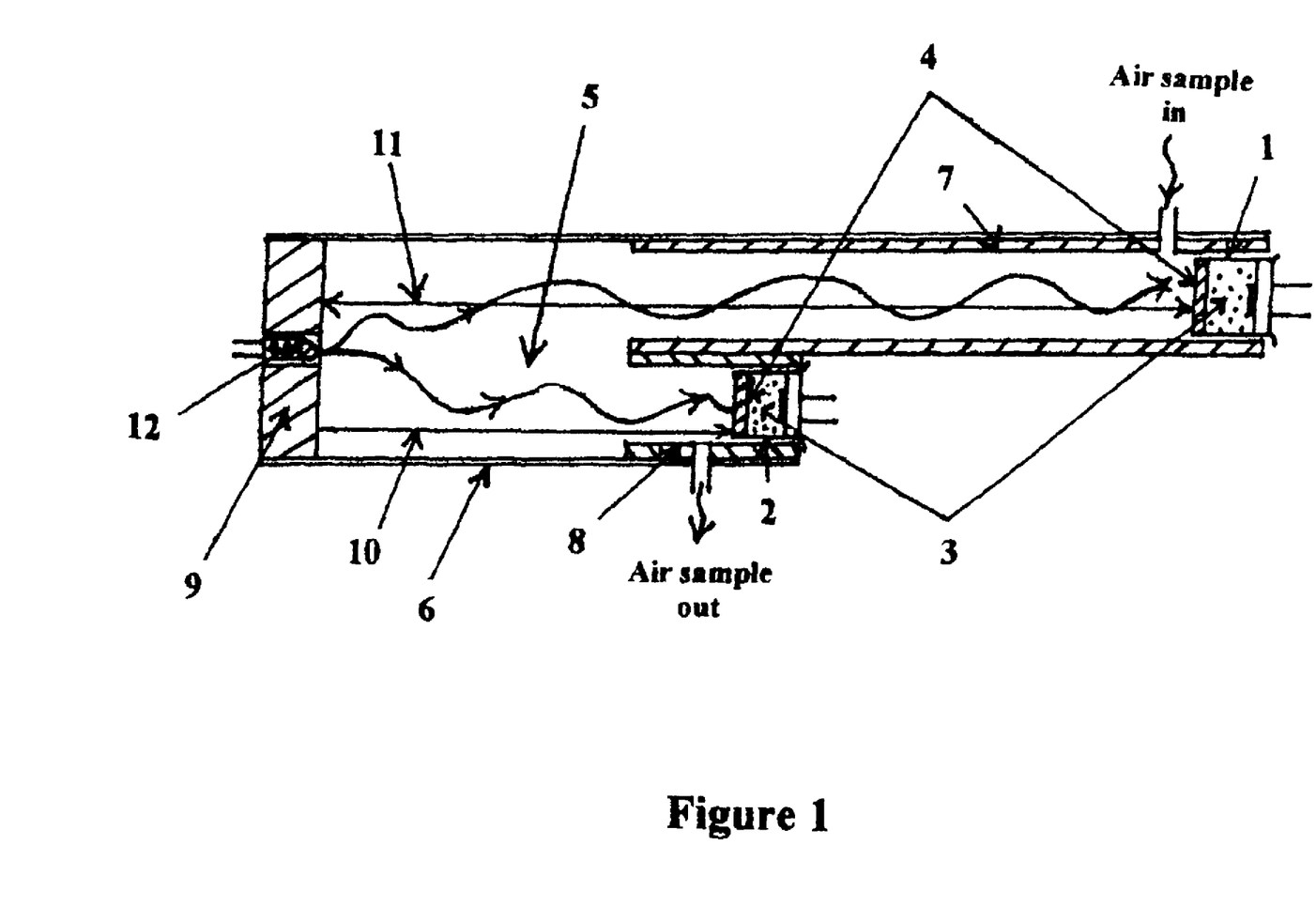
FIG. 1 shows the optical component layout for the Absorption Biased methodology for NDIR gas sensors.

FIG. 1 shows the optical component layout for the Absorption Biased methodology for NDIR gas sensors. As shown in FIG. 1, both the signal channel detector 1 and the reference channel detector 2 are entrapped with 100% dry nitrogen 3 and have the same narrow band-pass spectral filter 4 which is used to detect the gas of interest in the sample chamber 5. As an example, the filter designed to be used for the detection of CO2 gas will have a center wavelength (CWL)=4.26 ㄱ and a full width half maximum (FWHM)=0.14 ㄱ. Notice that both the detectors 1 and 2 are thermally connected to the entire sensor body 6 through their respective waveguides 7 and 8 and consequently they always share the same thermal platform with each other. In other words, the entire sensor body 6, which is in essence a composite of aluminum parts comprising the infrared source mount 9, sample chamber 5 and the waveguides 7 and 8, respectively, for the signal and reference channels, provides an excellent common thermal platform for detectors 1 and 2.

As shown in FIG. 1, the sample chamber path length LR, 10, associated with the reference channel is approximately one-half of the sample chamber path length LS, 11, associated with the signal channel. A common infrared source 12 is used to illuminate both the signal and the reference channels. The output of detector 1 for the signal channel is always less than that of the detector 2 for the reference channel irrespective whether or not there is any amount of the gas of interest in the sample chamber 5. The respective detector outputs can be determined by using the well-known Beer-Lambert Absorption Law for the particular gas of interest, the designed characteristics for the narrow band-pass filter 4 and the physical dimensions of LR 10 and LS 11.

Figure 2:
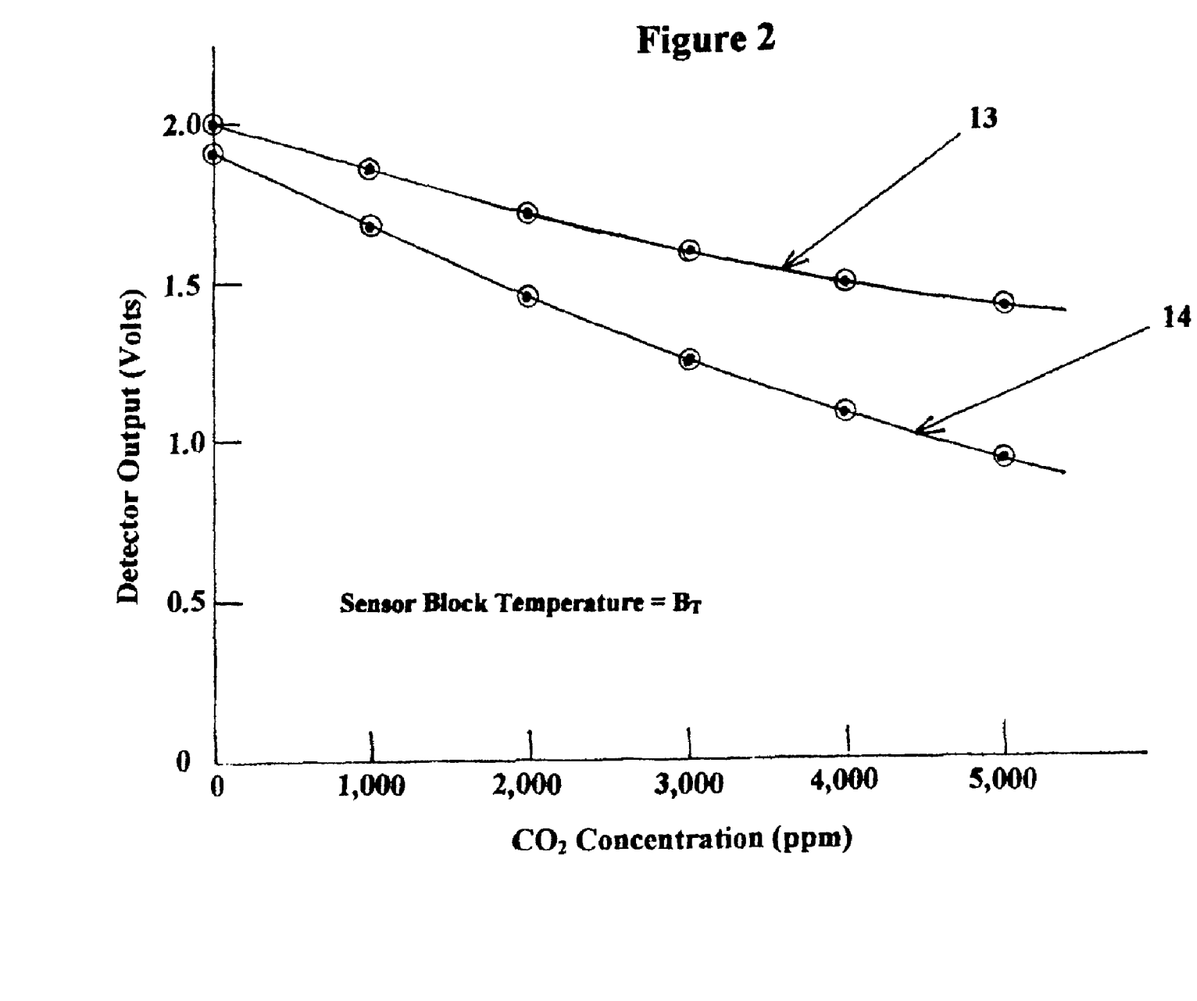
FIG. 2 shows respectively the output curves for the Reference and Signal channel detectors as a function of CO2 in the sensor sample chamber.
Figure 3:
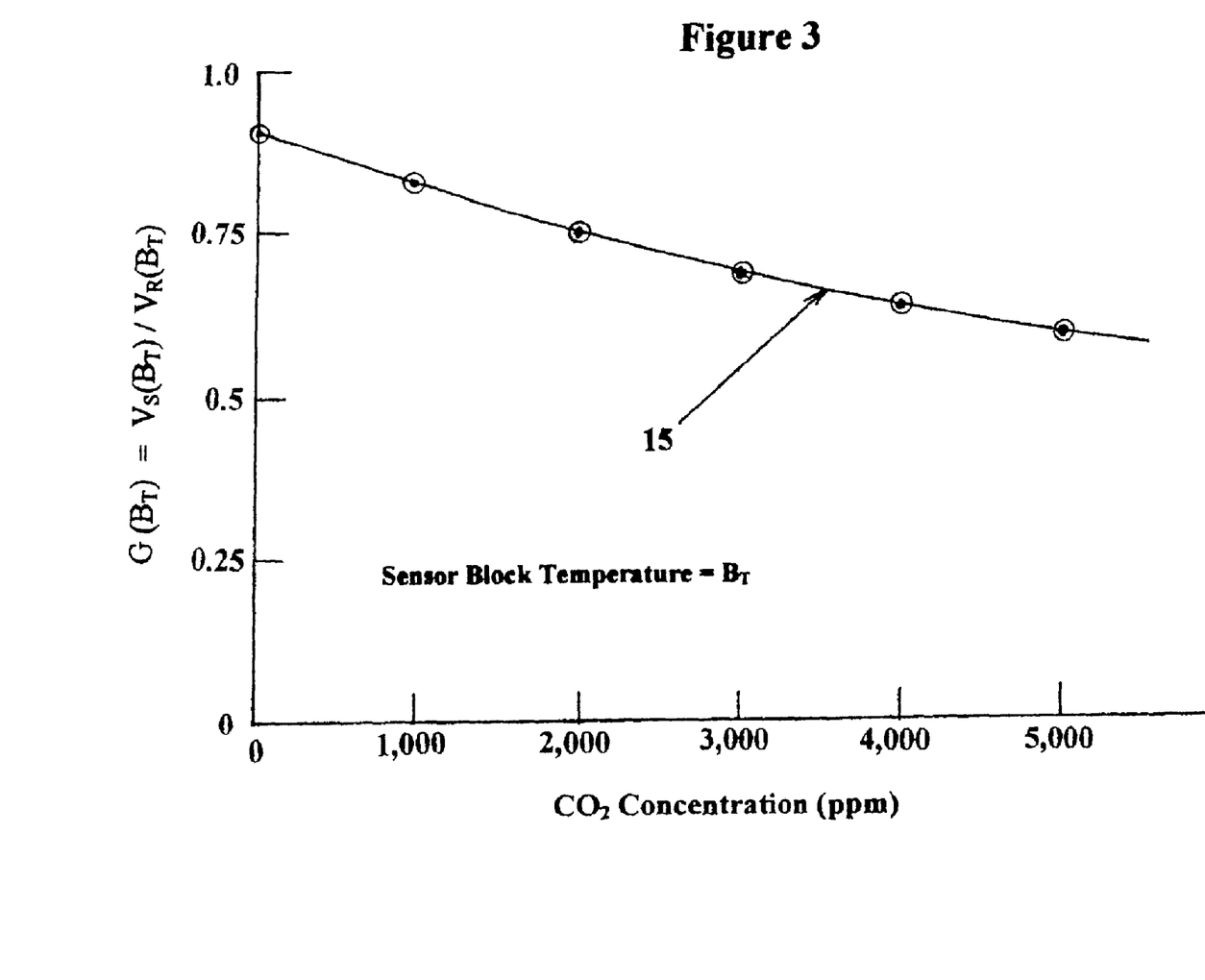
FIG. 3 shows the ratio of the output of the Signal channel detector over the Reference channel detector output at sensor block temperature BT as a function of CO2 in the sensor sample chamber.

FIG. 2 shows the graph 13 depicting the output VR(BT) of the reference channel detector 2 as a function of CO2 concentrations in the sample chamber 5. Graph 14 of FIG. 2 shows the output VS(BT) of the signal channel detector 1 as a function of CO2 concentrations in the same sample chamber. Note that both the outputs of the detectors are individually a function of the sensor block temperature BT, which is linked to the ambient temperature T wherein the sensor is located. Since the signal channel path length is longer than that for the reference channel, VS(BT) changes more than VR(BT) for any amount of CO2 in the sample chamber 5. An NDIR CO2 gas sensor implementing the Absorption Biased methodology processes the values for the ratio $$G(BT)=VS(BT)/VR(BT)$$

as a function of CO2 concentrations in the sample chamber 5. Such a functional relationship between G(BT) and the CO2 concentrations in the sample chamber 5 is the de facto calibration curve for the sensor as depicted by graph 15 in FIG. 3 for a particular sensor block temperature BT. Note that the value of G(BT) depends on the sensor block temperature BT and BT must therefore be kept unchanged during the calibration for the sensor when the concentrations of CO2 are made to vary in the sample chamber 5 in order to obtain the corresponding G(BT) values.

It is most important to note that the value of G(BT) other than being dependent upon the value of CO2 concentration in the sample chamber of the sensor and its block temperature BT, is invariant over time since both the signal and reference channels of the sensor have similar detectors with identical spectral filters and sharing the same thermal platform at BT. As a matter of fact, at any BT, the value of G(BT) is governed only by the NDIR gas absorption Physics for a particular gas of interest and is therefore invariant over time. However, while this is indeed true in theory, it is not quite exact in reality. This is because the components of the sensor will not be time invariant and their performance characteristics can and will inevitably change over time. For example, a sagging filament for the aging light bulb resulting in an output radiation pattern change or the responsivity of the signal channel detector changes differently over time from that of the reference channel detector, these changes are not related to any spectral changes of the source that are immune to causing any adverse effects to the calibration curve for the sensor implementing the Absorption Biased methodology. But when any of these component characteristics changes, they will affect the value of G(BT) and the calibration curve for the sensor will change resulting in the output drifts for the sensor over time.

The Absorption Biased methodology recognizes two distinct domains that constitute the sensor's realistic calibration curve. The first is the invariant NDIR gas absorption Physics domain discussed before and the second is the variant sensor component characteristics domain discussed below. As shown before, the invariant NDIR gas absorption Physics domain is represented by a functional relationship between $$G(BT)=VS(BT)/VR(BT)$$

and the concentrations of the gas of interest (e.g. CO2) in the sensor's sample chamber. The variant sensor component characteristics domain is represented by value of G(BT) when there is no gas of interest present in the sensor's sample chamber or G0(BT)=VS(BT)/VR(BT) . . . 0 concentration of gas of interest in sensor sample chamber Note that in this case the role of any NDIR gas absorption Physics for the gas of interest is eliminated since no gas is involved leaving G0(BT) strictly dependent only upon the sensor component characteristics.

By normalizing G(BT) with G0(BT) to form $$X(BT)=G(BT)/G0(BT)$$

and plotting the gas concentration (e.g. in ppm) as a function of X(BT), one combines the two domains together to formulate the realistic calibration curve for the sensor as $$P(ppm)=PX[X(BT)]=PX[G(BT)/G0(BT)] \quad (1)$$

Figure 4:
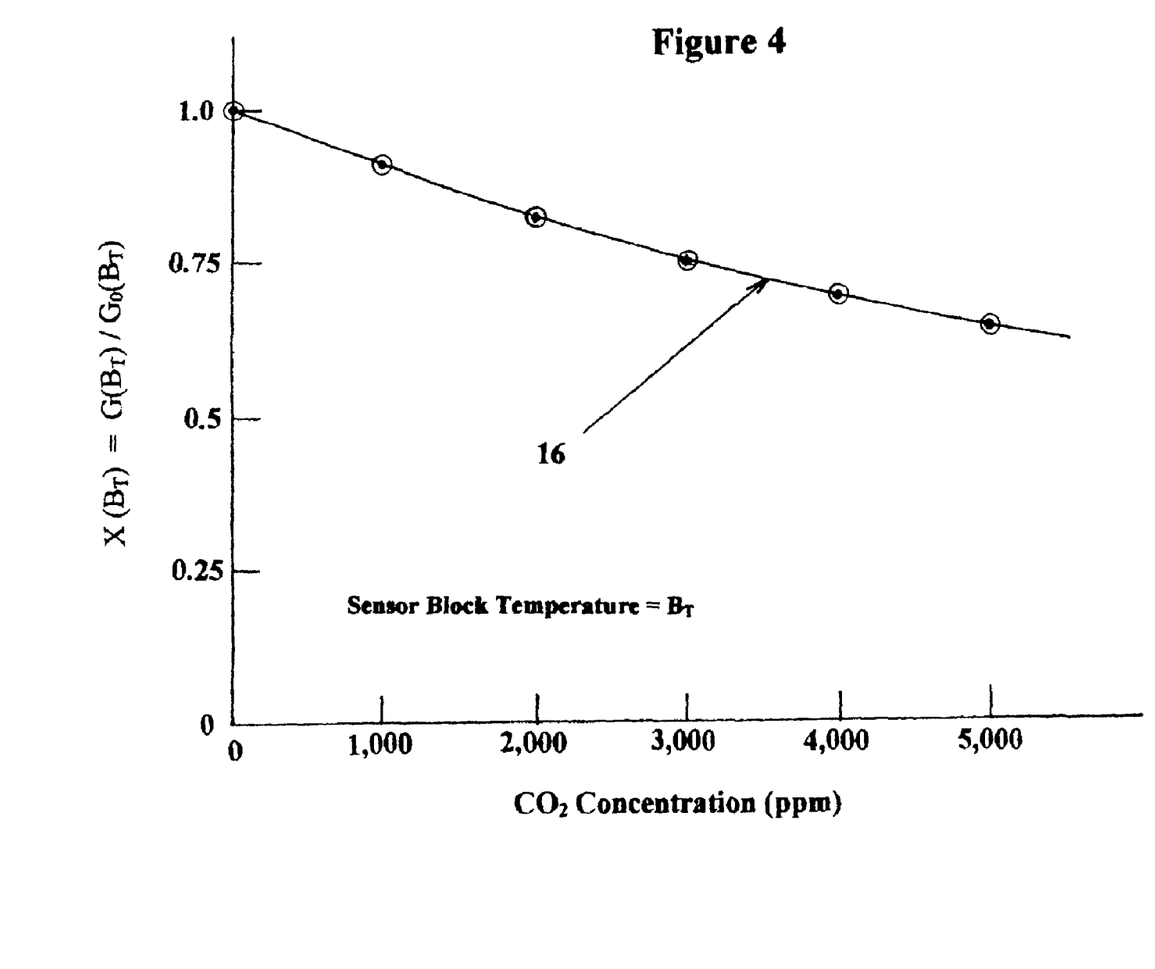
FIG. 4 shows the normalized ratio of the output of the Signal channel detector over the output of the Reference channel detector at sensor block temperature BT as a function of CO2 in the sensor sample chamber.
Figure 5:
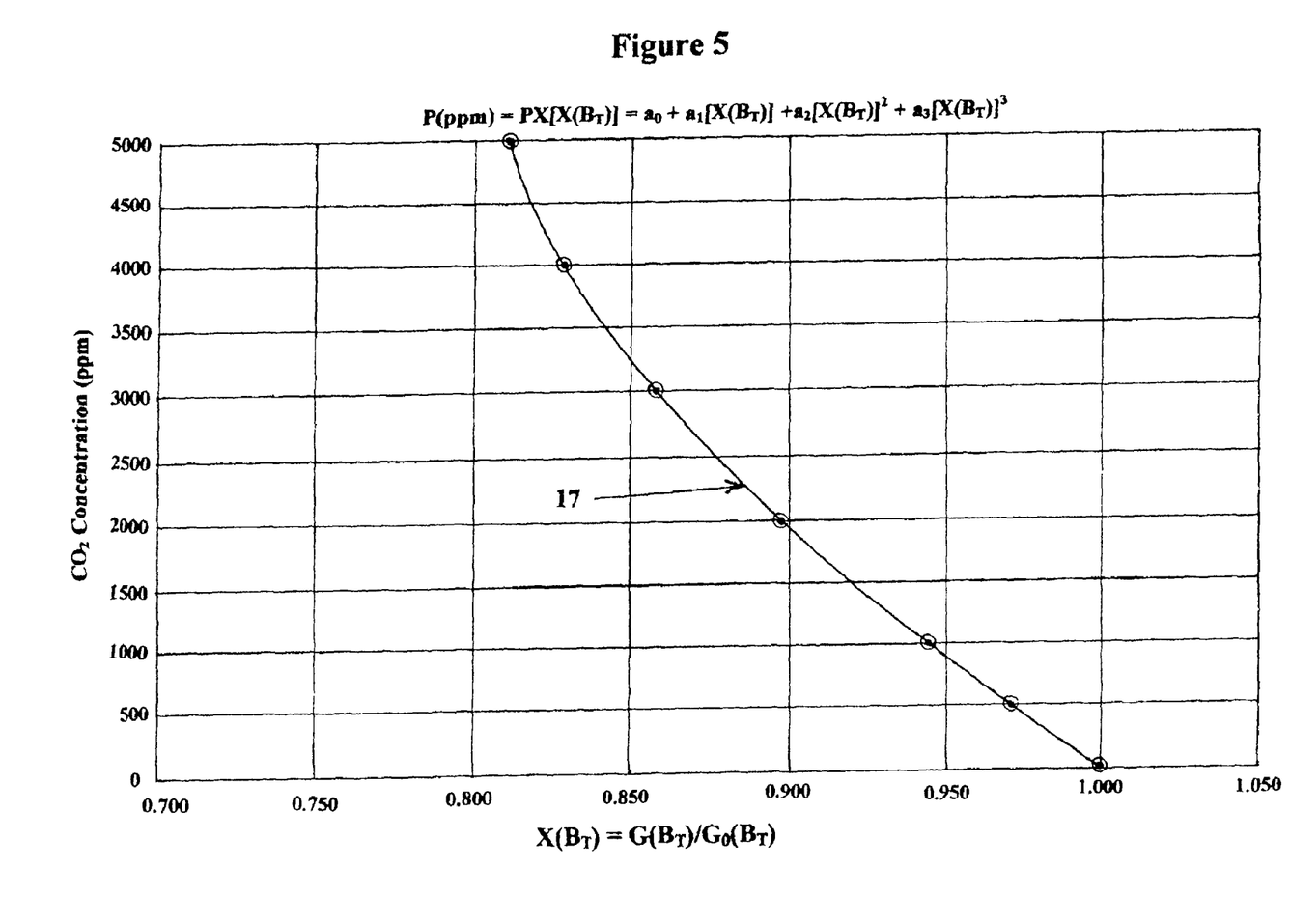
FIG. 5 depicts the sensor calibration curve expressed the CO2 concentration in the sample chamber for the Absorption Biased (AB) NDIR gas sensing methodology as a third order polynomial of the normalized ratio of signal output/reference output.
Figure 6:
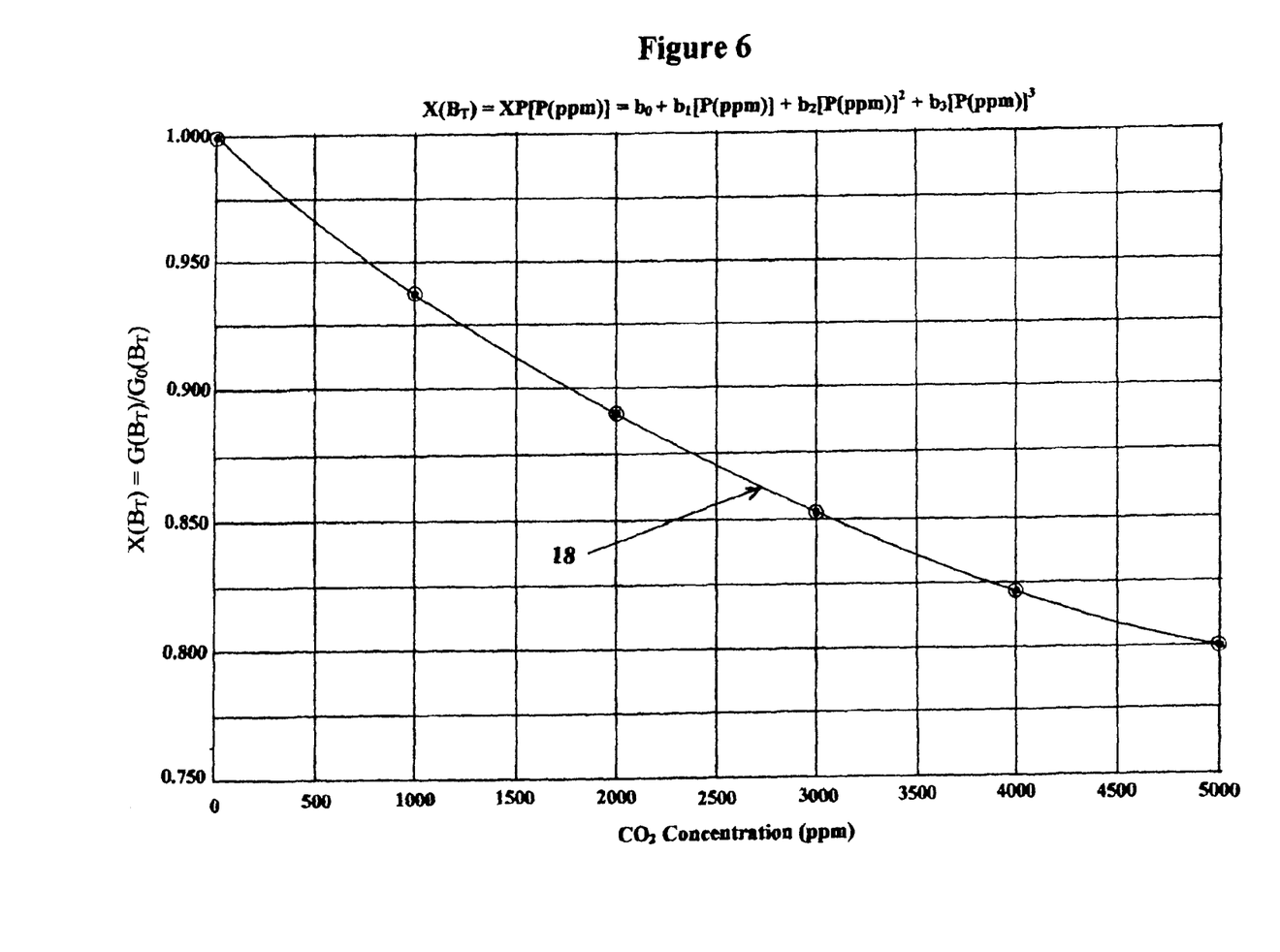
FIG. 6 depicts the sensor reverse calibration curve expressed the normalized ratio of signal output/reference output for the Absorption Biased (AB) NDIR gas sensing methodology as a third order polynomial of the CO2 concentration in the sample chamber.

By plugging in the value of X(BT) into the function PX, one can get the CO2 concentration in ppm. Graph 16 of FIG. 4 shows the de facto calibration curve for the sensor linking the value of X(BT) to the gas concentration (in this case CO2) in the sample chamber. Note the value of X(BT) starts off with unity when there is zero concentration of the gas (CO2) in the sample chamber. The function PX[X(BT)] can be expressed as a polynomial of X(BT) to the nth order (e.g. n=3 or the third order as depicted by graph 17 in FIG. 5). Conversely, the same plotted data could also be used to generate the inverse de facto calibration curve for the sensor or XP[P(ppm)] linking the CO2 gas concentration in the sample chamber P(ppm) to the value of X(BT). By plugging in the value of P(ppm) into the function XP, one can get the value of X(BT) or $$X(BT)=XP[P(ppm)] \quad (2)$$

XP[P(ppm)] can also be expressed as a third order polynomial of P(ppm) as depicted in graph 18 of FIG. 6. As stated earlier, at a particular BT of the sensor, the value of G(BT) is invariant as far as the gas absorption Physics is concerned. But since G0(BT) is also dependent upon BT, the calibration curve as shown in Equation (1) above for the sensor combining both the invariant Physics domain and the variant sensor components domain is valid only if G(BT) and G0(BT) are measured at the same temperature of BT. As a matter of fact, G(BT) can be determined at any temperature BT as long as G0(BT) is also determined at the same temperature for determining X(BT). Because of this fact, we must determine G0(BT) as a function of BT or $$G0(BT)=Q(BT) \quad (3)$$

where the function Q(BT) expresses the behavior of G0(BT) as a function of BT.

Now for the sensor to make a gas measurement, one first notes the sensor block temperature BT. One then measures G(BT) which is the ratio of the signal channel detector output over the reference channel detector output at BT. Using Equation (3) above to determine the value of G0(BT) at BT one then obtain the value of X(BT)=G(BT)/G0(BT). By plugging in the value of X(BT) into the polynomial PX of Equation (1) above, one obtains the gas concentration P(ppm) in the sample chamber. Conversely, one can also plug a known P(ppm) of gas value into the polynomial of Equation 2 above to obtain the corresponding value for X(BT) at temperature BT.

The formulation of the calibration curve in the NDIR Absorption Biased gas sensing methodology by separating it into two distinct domains, one being invariant and the other variant, leads to a very significant advantage when the sensor needs to be re-commissioned or recalibrated. In this case one needs only to refresh the variant domain without having to deal with the invariant domain. Therefore in the calibration curve expressed earlier in Equation (1) as $$P(ppm)=PX[X(BT)]=PX[G(BT)/G0(BT)] \quad (1)$$

only G0(BT) needs to be refreshed. Furthermore, one only needs 0 ppm gas or 100% dry nitrogen for the recalibration because the determination G0(BT) requires that there is zero concentration of gas in the sample chamber. But even the need for carrying a standard certified gas like 100% dry nitrogen in order to perform a re-commissioning or recalibration task can still be very labor intensive and cumbersome. It would be extremely advantageous if no standard certified gas is needed at all for this purpose. The advent of the Re-calibration methodology for Absorption Biased designed NDIR gas sensors as advanced by the present author in U.S. Application No. 13/149,738 (Wong, filed 31 May 2010) achieves this objective.

In this innovative technique, the gas concentration in the immediate neighborhood or surrounding of the sensor to be re-commissioned or recalibrated will first be accurately determined by a "Calibration Master". Needless to say, this so-called "Calibration Master" is a gas sensor that must live up to its name as being able to measure accurately the gas concentration in the vicinity of the sensor to be re-commissioned or recalibrated. (The Calibration Master can be another gas sensor whose accuracy has been checked or re-calibrated prior to the time it is being used by its operator to make rounds checking multiple gas sensors.) This information is then sent wirelessly via WiFi or via infrared under direct visual contact from the "Calibration Master" to the sensor in question. Using that information and a special algorithm within (described below), the sensor will know how to re-commission or recalibrate itself according to this information for the accurate gas concentration level of its environ that it receives from the Calibration Master.

There are three equations stored in every NDIR Absorption Biased methodology implemented gas sensor, namely $$P(ppm)=PX[X(BT)]=PX[G(BT)/G0(BT)] \quad (1)$$

$$G0(BT)=Q(BT) \quad (2)$$

$$X(BT)=XP[P(ppm)] \quad (3)$$

Upon receiving the correct gas concentration level of its ambience, the sensor in question calculates the correct Xc(BT) via the use of Equation (3) above. Meanwhile it also determines its own X(BT) by measuring G(BT) and looking up the correct value of G0(BT) at BT using Equation (2) above. Then it calculates the ratio X(BT)=G(BT)/G0(BT). If X(BT)=Xc(BT) to within a certain predetermined limit, nothing needs to be done or changed as the sensor is considered to stay accurately calibrated. However, if X(BT) is not equal to Xc(BT) within the predetermined accuracy limit, then G0(BT) must have changed because G(BT) is invariant. The new and correct G0c(BT) will be given by:

$$G0c(BT)=G(BT)/Xc(BT)$$

at temperature BT. With the use of the new G0c(BT) to take into account the change in time for the variant sensor component characteristics, the sensor is now recalibrated.

Since the same sensor might need to be rechecked later on in time and the ambient temperature as reflected by BT might be different, the Equation (2) for G0(BT) must also be modified with a correction factor given by $$F=G0c(BT)/G0(BT)$$

For subsequent use in time, Equation (2) above must be modified to include the correction factor F as shown below:

$$G0(BT)=F \times Q(BT) \quad (4)$$

in order to take into account the effect of the sensor block temperature BT.

Now that we understand the theoretical Physics principle behind the validity of what we now address as the "Effortless Re-Calibration" (ERC) technique specifically applicable only to Absorption Biased (AB) designed NDIR gas sensors, we will go into the procedural details and special equipment that is needed in order to carry out such a recalibration routine accurately all the time which is also the object of the current invention.

Figure 7:
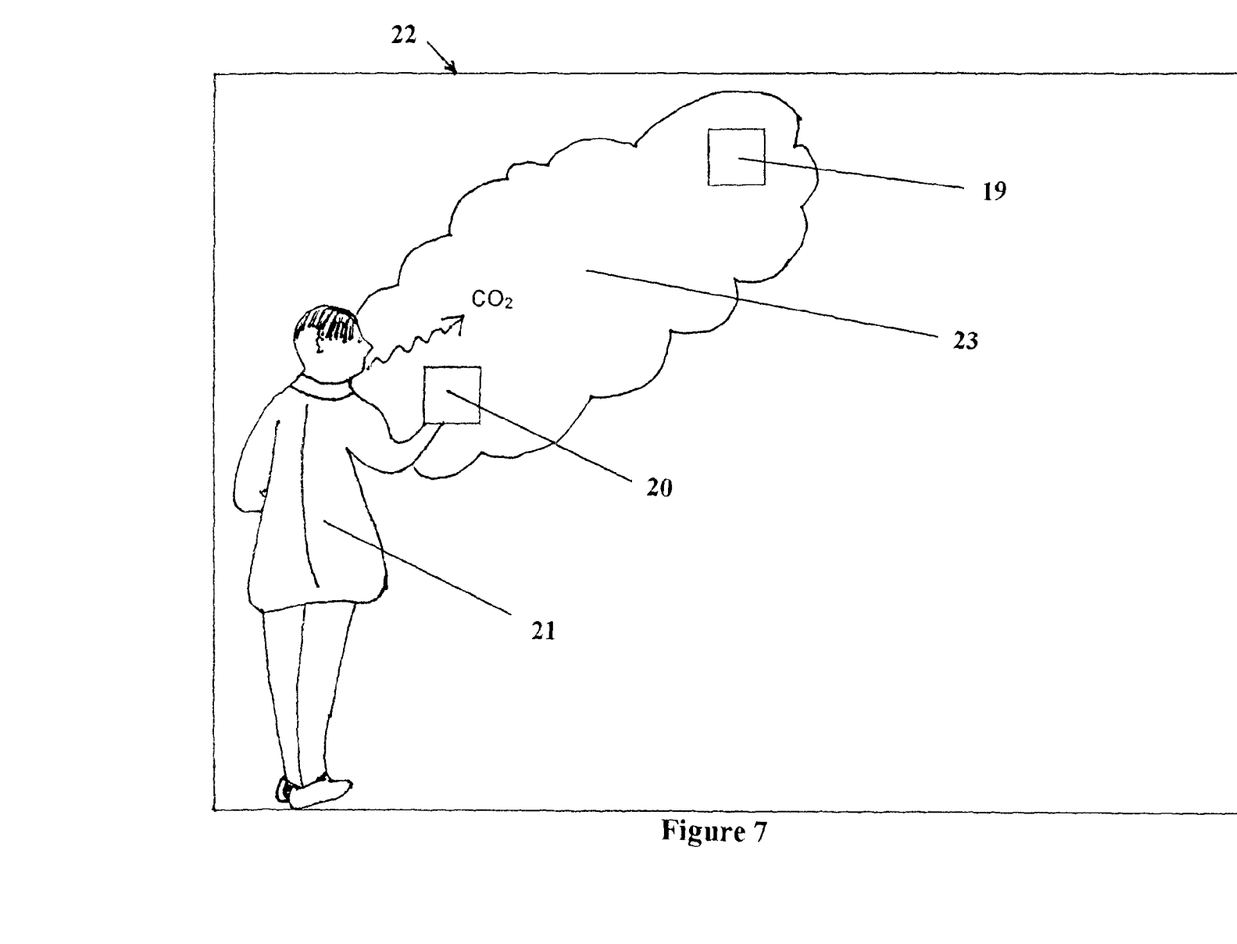
FIG. 7 portrays a typical scenario wherein an Absorption Biased (AB) designed NDIR gas sensor is being recalibrated by a Calibration Master using the Effortless Recalibration (ERC) technique without the use of an air sampler.

FIG. 7 portrays a typical scenario wherein an Absorption Biased (AB) designed NDIR gas sensor 19, e.g. a CO2 sensor, is to be recalibrated with a Calibration Master 20 held by an operator 21 using the Effortless Re-Calibration (ERC) technique described earlier. Operator 21 is standing just a few feet in front of sensor 19 which is hung roughly in the center and close to the top of a wall 22 which might typically be 20 ft. wide and 10 ft. tall. According to the teaching of the ERC technique, operator 21 using Calibration Master 20 is supposed to first accurately measure the concentration of the gas of interest (e.g. CO2) present in the environ shared commonly between it and sensor 19. Such an environ in this case is schematically represented by the volume of air space 23 as shown in FIG. 7. The next step in this ERC procedure is for the operator to obtain the concentration of the gas in the volume of air space 23 as measured by sensor 19 via sending a remote command to it wirelessly using, e.g., WiFi or direct sight infrared, from Calibration Master 20. If operator 21 finds out that the gas concentration level as obtained from the sensor 19 and that from the Calibration Master 20 do not agree to within a predetermined accuracy limit, the operator would proceed to send another command to sensor 19 from Calibration Master 20 in order to recalibrate it using the value obtained by Calibration Master 20 according to the teaching of the ERC technique described earlier. (Of course, Calibration Master 20 can be programmed so that it automatically sends a recalibration command upon detection of one or more grounds that trigger the sending of such a command.)

Although the ERC maneuver to recalibrate sensor 19 just described is technically correct, it might not be very accurate at all. The reason is that the concentration of the gas of interest in the common environ of air space 23 (see FIG. 7) as measured by sensor 19 and the Calibration Master 20 might not always the same. The basic assumption that the concentration level of the gas surrounding the sensor 19 is the same as that surrounding the Calibration Master 20 can only be true if there is no air flow of any kind in the air space 23 shared by the two sensors during the recalibration maneuver. Furthermore, since this air space 23 is closer to the operator 21 who exhales quite a bit of $CO_2$ gas into air space 23 while working, the concentration of the gas of interest in the shared air space 23 may be non-uniform with higher gas concentration level leaning towards the operator 21 holding the Calibration Master 20. This gas concentration non-uniformity plus the fact that the still air condition in air space 23 during the recalibration routine cannot always be guaranteed in real life situations lead to the inevitable conclusion that performing the ERC this way might not always be accurate.

Figure 8:
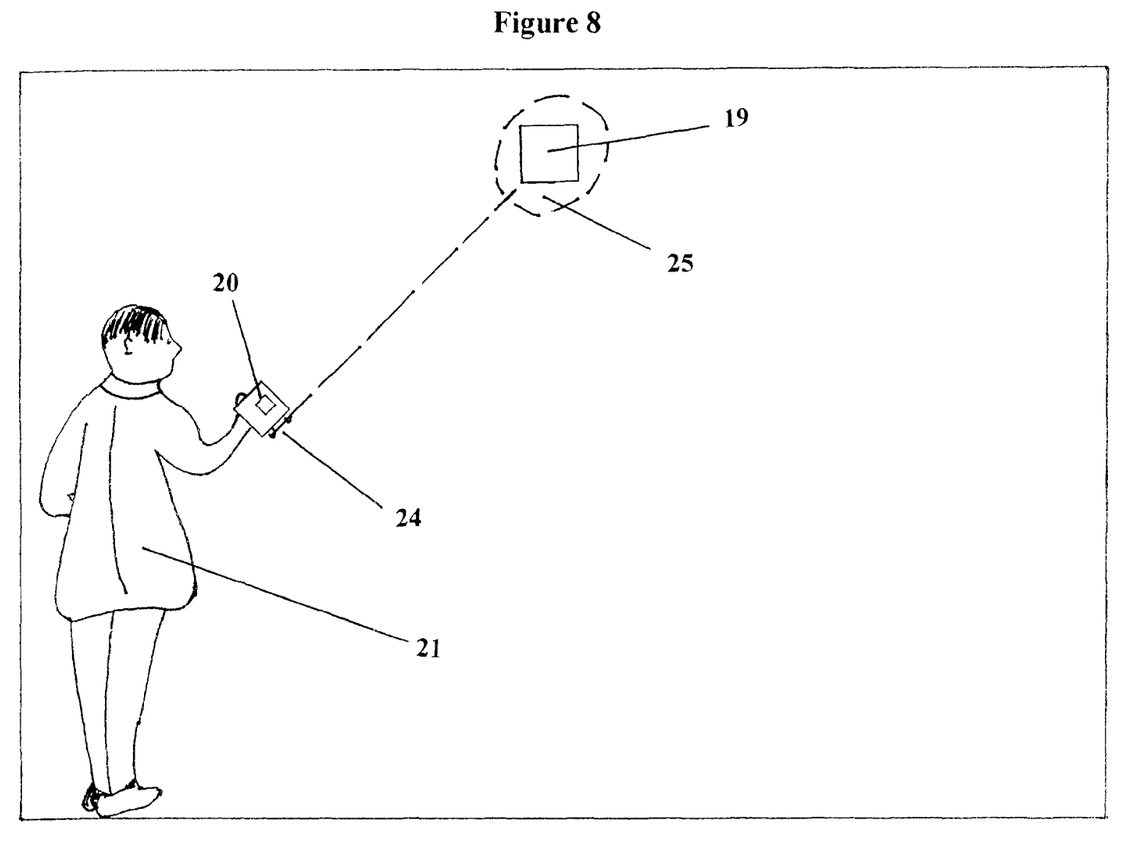
FIG. 8 portrays a typical scenario wherein an Absorption Biased (AB) designed NDIR gas sensor is being recalibrated by a Calibration Master using the Effortless Recalibration (ERC) technique with the use of an air sampler.

The current invention remedies potential shortcomings of the above situation by providing a specially designed air sampler 24 built into Calibration Master 20 as illustrated in FIG. 8 in order that both the sensor 19 which is to be recalibrated and the Calibration Master 20 can now measure the concentration level of the gas of interest in the same close environ air space 25 immediately close to sensor 19. Consequently if sensor 19 correctly reads the gas concentration value in close environ air space 25, it should be substantially the same value as that measured by Calibration Master 20 held by operator 21 with the aid of the special air sampler 24. With the use of this air sampler 24, the potential error that the sampled air surrounding sensor 19 is not the same as that surrounding the Calibration Master 20 is eliminated, or at least reduced to the point that it will not interfere with the recalibration procedure.

Figure 9:
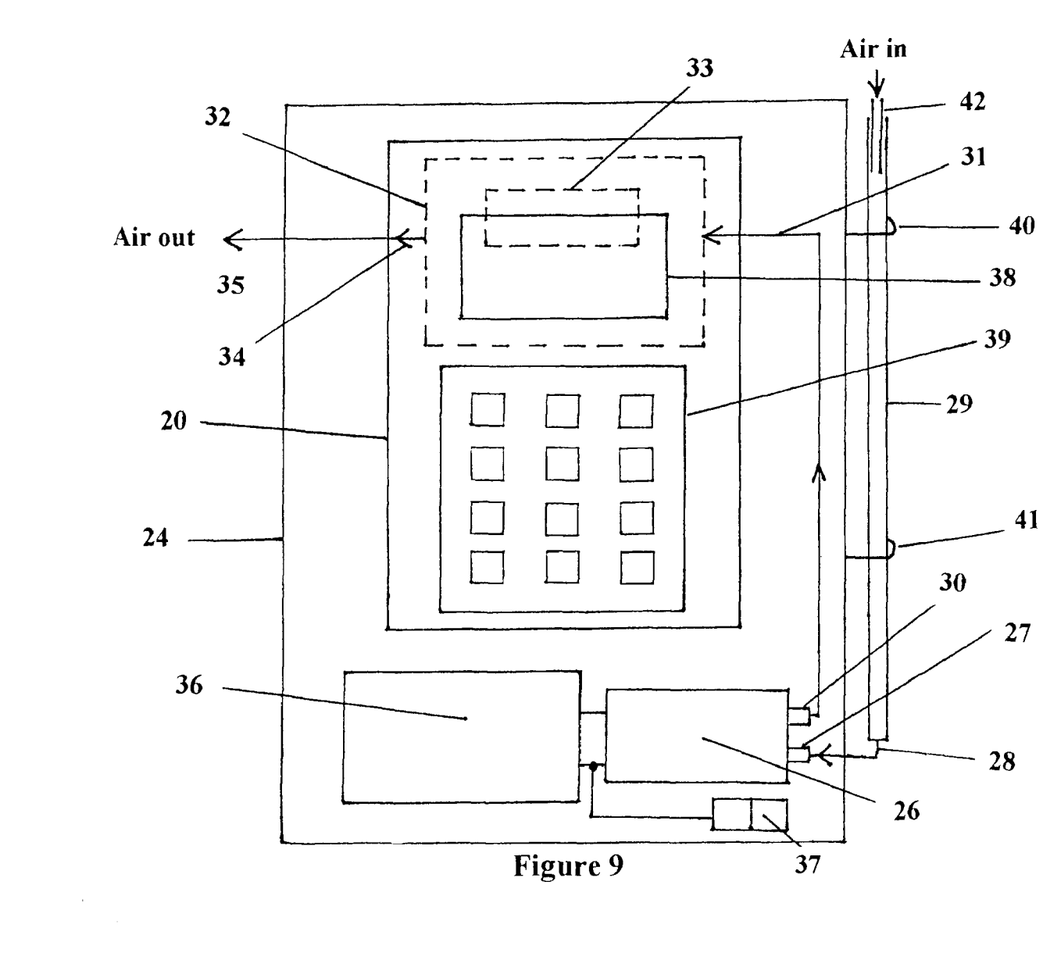
FIG. 9 depicts the component layout and construct of a specially designed air sampler guaranteeing at all times the accuracy of using the ERC technique to recalibrate an AB designed NDIR gas sensor with a Calibration Master.
Figure 10:
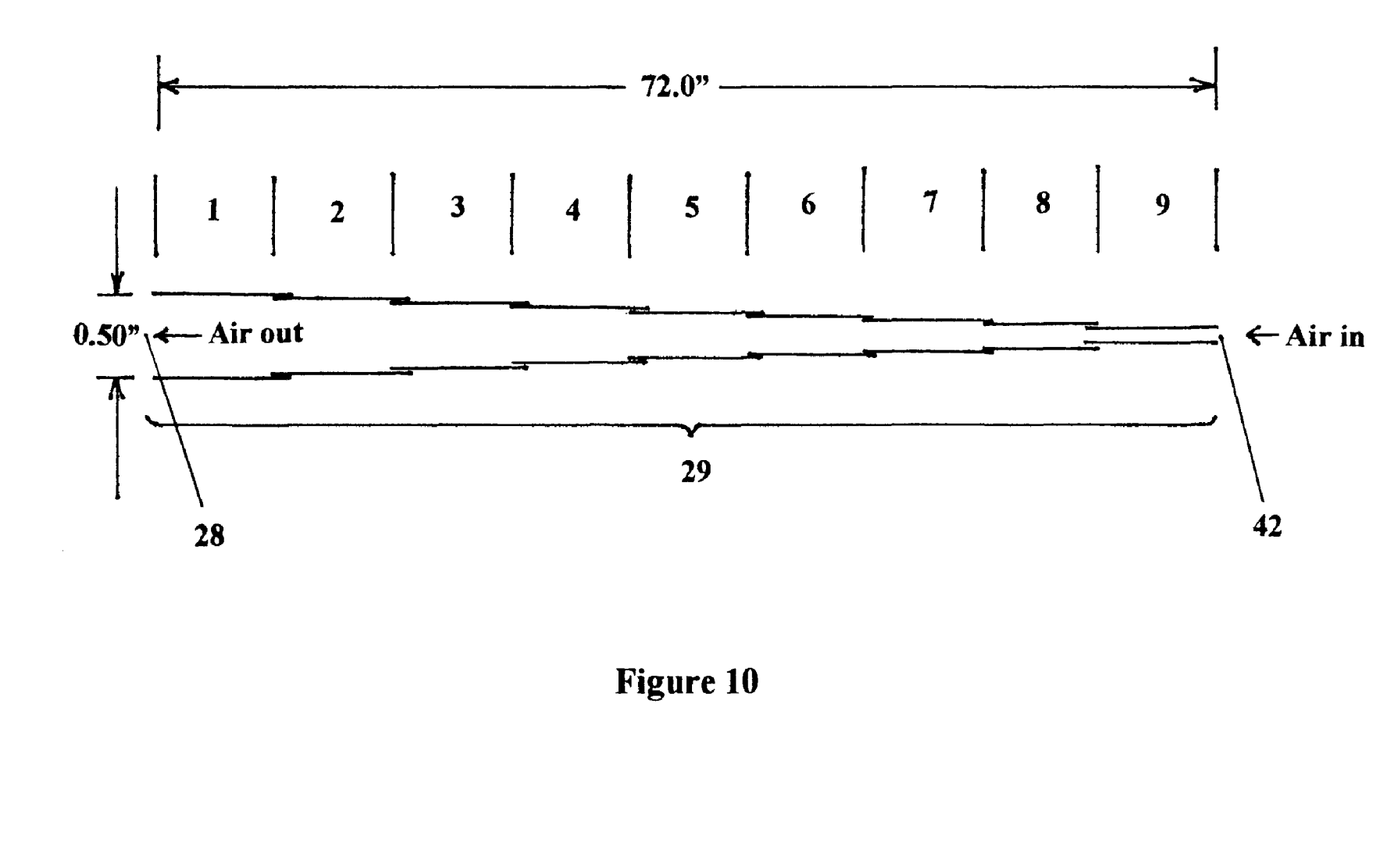
FIG. 10 shows the details of an air-tight telescopic tube which is part of the specially designed air sampler.

FIG. 9 portrays the details of the components layout for an especially preferred embodiment of a specially designed air sampler 24 encompassing the Calibration Master 20 in the same package. The specially designed air sampler 24 comprises a small air pump 26 whose inlet 27 is connected to one end 28 of an air-tight telescopic sampling tube 29 (see FIG. 10). Outlet 30 of air pump 26 is connected to inlet 31 of an air-tight confined space 32 wherein an AB designed NDIR gas sensor 33 is located. Outlet 34 of confined space 32 leads to free space 35 outside of specially designed air sampler 24. Air pump 26 is powered by a battery pack 36 and controlled by an ON/OFF switch 37 all located inside the air sampler unit 24. Also confined inside air sampler unit 24 is Calibration Master 20 whose printed circuit board (PCB) (not shown in FIG. 9) interfaces with AB designed NDIR gas sensor 33 on one side and a LCD display 38 and a keypad 39 on the other. Whereas LCD display 38 shows operator 21 of Calibration Master 20 what is going on at any one time, keypad 39 allows operator 21 to issue functional commands to Calibration Master 20 in order for it to carry out the ERC routine.

An air-tight telescopic sampling tube 29 (see FIG. 10), when not in use, is lodged by two clamps 40 and 41 located on the right-hand-side of air sampler unit 24. Unlike an ordinary telescopic tubing where the joints of its sections may not normally designed to be air-tight, the telescopic tubing 29 (see FIG. 10) of air sampler 24 is, in an especially preferred embodiment, specifically designed to have substantially air-tight sections so that air does not get into air sampler unit 24 during sampling except through inlet 42 of telescopic sampling tube 29 (see FIGS. 9 and 10). The air-tight telescopic sampling tube 29 might be 6 ft. long when fully extended with 9 sections and an outside diameter of 0.5". When all its sections are drawn back, its length is around 8". In theory this air-tight sampling tube 29 can be of any length and any diameter as long as it is convenient to use for air sampling under all circumstances.

So far the ERC procedure has been described in terms of how it can be accomplished in the field. It should be noted that the ERC procedure can be accomplished very quickly, without the need for using standard gasses, which greatly reduces the cost of the procedure. In practice, it is important to realize that the ERC procedure allows a technician to check calibration of large numbers of sensors in short periods of time, a limiting factor being the time necessary to move between sensors and a short amount of time needed for an ERC procedure.

In an especially preferred embodiment of the ERC procedure, each gas sensor has a unique identification number. A Calibration Master can address a particular gas sensor via its unique ID number and can request instantaneous data from it in order to ascertain whether the gas sensor is accurate.

To increase the efficiency of the ERC procedure, in an especially preferred embodiment, software is included in Calibration Master 20 (e.g., in processor memory or other memory media) to facilitate the ERC process and also allow Calibration Master 20 to interact with a computer (e.g., by use of the Internet, a LAN, a WAN or hardware device) where information from Calibration Master 20 can be collected and utilized with one or more computer program modules to track compliance with scheduled calibration checks. Thus, for example, each time an ERC procedure is performed, Calibration Master 20 can create and store a data file containing desired information such as the unique identifier of the gas sensor being checked, the gas concentration detected by the gas sensor, the date and time of the procedure, whether the gas sensor was recalibrated and any other desired information. If desired, automatic reports documenting the ERC procedure, and its results, can be generated, stored or sent to one or more additional locations electronically, such as through, for example, an Internet connection. Because the information used to generate such results is stored electronically, human error is minimized and, if desired, the system can be configured with sufficient safeguards so as to prevent doctoring of calibration results, thus guaranteeing better information regarding long term stability results of gas sensors subjected to the ERC procedure.

It is also worth pointing out that a Calibration Master can be configured so that it can be used to test multiple gas sensors used to sense different types of gasses or a single gas sensor that can detect multiple gasses. For example, a single gas sensor might be configured so that it can detect both $CO_2$ and water vapor, and a single Calibration Master can be designed to calibrate the sensor for both gasses.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A method that uses an absorption biased ("AB") non-dispersive infrared ("NDIR") gas sensor having a sample chamber used to detect a sample gas, comprising:
   obtaining an air sample from a close environ air space in which the AB NDIR gas sensor is located;
   using a calibration master NDIR gas sensor to calculate a calibration master gas concentration ("PCM") of the sample gas within the close environ air space from the air sample;
   calculating a gas concentration ("P") of the sample gas within the close environ air space detected by the AB NDIR gas sensor through use of a calibration curve for the AB NDIR gas sensor, said calibration curve being obtained from a gamma ratio ("G") that has been normalized by the gamma ratio when no sample gas is present in the sample chamber ("G0"), G being the ratio of a signal channel output ("VS") of the NDIR gas sensor divided by a reference channel output ("VR") of the NDIR gas sensor;
   and
   if a recalibration condition is detected, recalibrating the NDIR gas sensor by comparing P to PCM and adjusting G0 based upon a reversed calibration curve algorithm;
   wherein the AB NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel pathlength and the AB NDIR gas sensor has no moving parts for effecting the interposition of spectral filters or an absorbing cell or a non-absorbing cell to create both the signal channel and the reference channel.

2. The method of claim 1, wherein the close environ air space is accessed by the calibration master NDIR gas sensor through use of an air sampler.

3. The method of claim 1, wherein the close environ air space is accessed by the calibration master NDIR gas sensor through use of a substantially air-tight telescopic sampling tube.

4. The method of claim 1, wherein the calibration master NDIR gas sensor communicates with the AB NDIR gas sensor.

5. The method of claim 4, wherein the calibration master NDIR gas sensor sends the AB NDIR gas sensor a recalibration command that causes the AB NDIR gas sensor to be recalibrated when the recalibration condition is detected.

6. The method of claim 4, wherein the calibration master creates a record of P, PCM, an identifier that uniquely identifies the AB NDIR gas sensor and a date associated with when the air sample was obtained.

7. The method of claim 1, wherein the calibration master NDIR gas sensor communicates wirelessly with the AB NDIR gas sensor.

8. The method of claim 1, wherein the recalibration condition is comprised of a difference between P and PCM that exceeds a preselected threshold.

9. The method of claim 1, wherein the calibration master is comprised of a second AB NDIR gas sensor.

10. The method of claim 1, wherein the air sample is obtained substantially simultaneously with when P is calculated.

11. A system, comprising:
   an absorption biased ("AB") non-dispersive infrared ("NDIR") gas sensor having a sample chamber used to detect a sample gas;
   a calibration master NDIR gas sensor that can calculate a calibration master gas concentration ("PCM") of the sample gas from an air sample obtained within a close environ air space; and
   an air sampler for obtaining the air sample from the close environ air space;
   wherein the AB NDIR gas sensor is located proximate the close environ air space; and
   wherein the AB NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel pathlength and the AB NDIR gas sensor has no moving parts for effecting the interposition of spectral filters or an absorbing cell or a non-absorbing cell to create both the signal channel and the reference channel.

12. The system of claim 11, wherein the calibration master NDIR gas sensor communicates with the AB NDIR gas sensor.

13. The system of claim 12, wherein the calibration master NDIR gas sensor sends the AB NDIR gas sensor a recalibration command that causes the AB NDIR gas sensor to be recalibrated when a recalibration condition is detected.

14. The system of claim 12, wherein the calibration master creates a record of P, PCM, an identifier that uniquely identifies the AB NDIR gas sensor and a date associated with when the air sample was obtained.

15. The system of claim 11, wherein the calibration master NDIR gas sensor communicates wirelessly with the AB NDIR gas sensor.

16. The method of claim 11, wherein the calibration master is comprised of a second AB NDIR gas sensor.

* * * * *